(12) United States Patent
Hiroi et al.

(10) Patent No.: US 7,049,587 B2
(45) Date of Patent: May 23, 2006

(54) APPARATUS FOR INSPECTING A SPECIMEN

(75) Inventors: Takashi Hiroi, Yokohama (JP);
Masahiro Watanabe, Yokohama (JP);
Asahiro Kuni, Tokyo (JP); Maki Tanaka, Yokohama (JP); Munenori Fukunishi, Yokohama (JP); Hiroshi Miyai, Hitachi (JP); Yasuhiko Nara, Hitachinaka (JP); Mitsunobu Isobe, Machida (JP)

(73) Assignee: Hitachi, Ltd., Tokyo (JP)

( * ) Notice: Subject to any disclaimer, the term of this patent is extended or adjusted under 35 U.S.C. 154(b) by 422 days.

(21) Appl. No.: 10/079,428

(22) Filed: Feb. 22, 2002

(65) Prior Publication Data

US 2003/0063792 A1 Apr. 3, 2003

Related U.S. Application Data

(63) Continuation of application No. 10/062,666, filed on Feb. 5, 2002.

(30) Foreign Application Priority Data

Sep. 28, 2001 (JP) ............................. 2001-298910

(51) Int. Cl.
*G01N 23/00* (2006.01)
*G21K 7/00* (2006.01)
(52) U.S. Cl. ..................................... 250/310
(58) Field of Classification Search ............... 250/311, 250/310; 382/149; 364/188, 468.17
See application file for complete search history.

(56) References Cited

U.S. PATENT DOCUMENTS

| | | | | |
|---|---|---|---|---|
| 5,761,064 A | * | 6/1998 | La et al. | 700/110 |
| 5,777,327 A | * | 7/1998 | Mizuno | 250/310 |
| 6,047,083 A | * | 4/2000 | Mizuno | 382/141 |
| 6,097,887 A | * | 8/2000 | Hardikar et al. | 717/105 |
| 6,476,913 B1 | * | 11/2002 | Machida et al. | 356/394 |
| 6,539,106 B1 | * | 3/2003 | Gallarda et al. | 382/149 |
| 6,919,564 B1 | * | 7/2005 | Nara et al. | 250/310 |

* cited by examiner

*Primary Examiner*—Nikita Wells
*Assistant Examiner*—Kalimah Fernandez
(74) *Attorney, Agent, or Firm*—Antonelli, Terry, Stout and Kraus, LLP.

(57) ABSTRACT

Conventionally, defect data outputted by an inspection system comprised only characteristic quantitative data, such as coordinate data, area, and projected length, and only the coordinate data for moving to a defect location could be utilized effectively. By contrast, by using image data in addition to characteristic quantitative data as the defect data for an inspection system, the retrieval of image data via an outside results confirmation system is made possible. Further, for defect data of a plurality of substrates, it is possible to display a defect image during inspection by the fact that similar defects are retrieved via images and retrieval results are displayed as trends, which makes it possible to display a defect image during inspection by searching similar defects on images and displaying them as a trend, and designating a substrate on the trend, thereby displaying the defect map thereof and designating a defect on the defect map.

20 Claims, 7 Drawing Sheets

APPARATUS FOR INSPECTING A SPECIMEN

CROSS REFERENCE TO RELATED APPLICATION

This is a continuation of application Ser. No. 10/062,666, filed Feb. 5, 2002, entitled "PATTERN INSPECTION METHOD AND SYSTEM THEREFOR", by T. HIROI, the contents of which are incorporated herein by reference.

BACKGROUND OF THE INVENTION

The present invention is related to a system for the manufacture of a substrate having a circuit pattern, such as a semiconductor device or liquid crystal display; and, more particularly, the invention relates to technology for inspecting a substrate pattern during fabrication.

Conventional optical or electron beam pattern inspection systems are described in Japanese Patent Laid-open No. H5-258703 and Japanese Patent Laid-open No. H11-160247.

FIG. 1 shows the constitution of a system disclosed in Japanese Patent Laid-open No. H5-258703 as an example of an electron beam pattern inspection system. In this system, an electron beam 2 from an electron beam source 1 is deflected in the X direction by a deflector 3 and is irradiated onto a target substrate 5 via an object lens 4, while a stage 6 is simultaneously made to move continuously in the Y direction. Secondary electrons 7 from the target substrate 5 are detected by a detector 8, and the detected signal is converted from analog to digital by an analog-to-digital (A/D) converter 9 to form a digital image, which is compared in an image processing circuit 10 to a digital image of a place that can be expected to be the same as the original, a place that differs is detected as a pattern defect 11, and the location of the defect is established.

FIG. 2 shows the constitution of the system disclosed in Japanese Patent Laid-open No. H11-160247 as an example of an optical inspection system. In this system, a light from a light source 21 is irradiated onto a target substrate 5 via an object lens 22, and a reflected light is detected by an image sensor 23 at that time. By repeatedly detecting the reflected light while a stage 6 moves at a constant speed, an image is detected as a detected image 24, and this image 24 is stored in memory 25. The detected image 24 is compared with a memory stored image 27, which can be expected to have the same pattern as the detected image 24, and if the patterns are identical, the detected image 24 is determined to be a normal portion. However, but if the patterns differ, this difference is detected as a pattern defect 11, and the defect location is established.

As an example, FIG. 3 shows a layout of a wafer 31 which represents a target substrate 5. Dies 32, which are ultimately cut apart to yield individual products of the same variety, are formed on wafer 31. Stage 6 is moved along a scanning line 33, and an image of the stripe region 34 is detected. When the present detection location A is at 35, an image of detection location B 36 in memory 25 is extracted as a stored image 27, and the two images are compared. Thereby, detection location A 35 is compared against a pattern that can be expected to be an identical pattern. Here, memory 25 possesses a capacity capable of holding an image that can be expected to be an identical pattern, that is used repeatedly in a ring shape to form an actual circuit.

In the case of both inspection systems, to confirm the results of the inspection, the inspected data is outputted to a review system. Thereafter, the wafer is transferred to and set on a table of the review system to review defects detected by the inspection system. In the review system, the defect to be reviewed is placed in a viewing field of the review system by using the inspected data outputted from the inspection system. Then, the image is visually observed to judge whether or not it has an actual defect or to infer what could have caused it. In such a reviewing method, a vast amount of image data acquired during the inspection is not effectively used.

SUMMARY OF THE INVENTION

The present invention is constituted such that an image of a defect portion, which is similar to an image of a defect portion specified on the basis of inspection results outputted by an inspection system, and the defect portion image data thereof, is retrieved, and the conditions for the occurrence of a specific mode defect, which have occurred in the past, can be identified by displaying the retrieval results, so as to enable identification.

A first system according to the present invention will be explained. A constitution of a system that uses an electron beam will be considered, but there is substantially identical to a system which utilizes another type of charged particle.

As seen in FIG. 4, the system is constituted from an electron beam source 1 for generating an electron beam 2; a deflector 3 for deflecting the electron beam 2; an object lens 4 for converging the electron beam 2 onto a target substrate 5; and a stage 6 for holding, scanning and positioning the target substrate 5. A detector 8 is grounded for detecting secondary electrons 7 emitted from the target substrate 5; and, an A/D converter 9 operates to convert a detected signal from analog to digital to form a digital image. An image processing circuit 110 compares the digital image against a digital image of a location that can be expected to be substantially identical and detects a location that is different as a pattern defect 11. Defect data storing means 201 operates to store defect data 200 comprising the defect location and image data of the pattern defect 11; and data outputting means 203 outputs the stored defect data 202 to either a network or a storage medium. An inputting means 205 is provided for inputting defect data 202 related to a plurality of wafers, which was outputted to data transferring means 204 by data outputting means 203; and defect data storing means 206 stores the inputted defect data. A defect map 207 operates to display defect location data of the wafer on a display screen and selecting means 208 selects a specific defect on the defect map 207. Image displaying means 209 displays the image of the selected defect data in an image format. Search command means 210 is provided for issuing a command for retrieving, from the defect data group a defect image that is similar to a displayed image; and image retrieving means 211 operates to retrieve an image having image data that is similar to a displayed image.

The electron beam 2 from electron beam source 1 is irradiated onto target substrate 5 via object lens 4, and generated secondary electrons 7 are detected by the detector 8. In this operation, the electron beam 1 is deflected by deflector 3, image data is formed by using stage 6 for scanning target substrate 5, the image data detected by the detector is converted from analog to digital by A/D converter 9, so that a digital image is formed. Image processing circuit 110 compares this digital image with a digital image which is expected to be substantially identical, and detects a difference between the two images as a pattern defect 11. Defect data 200, comprising the defect location and image data of the detected pattern defect 11, is stored in defect data storing means 201, and stored defect data 202 is outputted by data outputting means 203 as necessary to information transferring means 204 in the form of either a network or a storage medium.

Defect data 202 of a plurality of wafers, which is outputted from outputting means 203, is inputted by inputting means 205 and is stored in a storing means 206, and the defect location data of the inputted defect data is displayed on defect map 207. When a specific defect on the defect map is selected by selecting means 208, an image of the selected specific defect is displayed on image displaying means 209. When a command is issued by search command means 210, a defect image similar to the displayed image is retrieved from among the stored defect data stored in the storing means 206 by image retrieving means 211, and the retrieval results are reflected in defect map 207. Retrieval results can be checked as needed by issuing a command via selecting means 208. The frequency at which similar defects occur can be checked by displaying in the time-series format shown in FIG. 5, a display format of defect map 207. In accordance therewith, the image data acquired at inspection time can be utilized effectively.

These and other objects, features and advantages of the invention will be apparent from the following more particular description of preferred embodiments of the invention, as illustrated in the accompanying drawings.

DESCRIPTION OF THE PREFERRED EMBODIMENTS

The embodiments of the present invention will be explained hereinbelow using specific figures. The overall system will be explained first, and then the respective parts of the system will be explained.

(Overall System)

Figure 6:
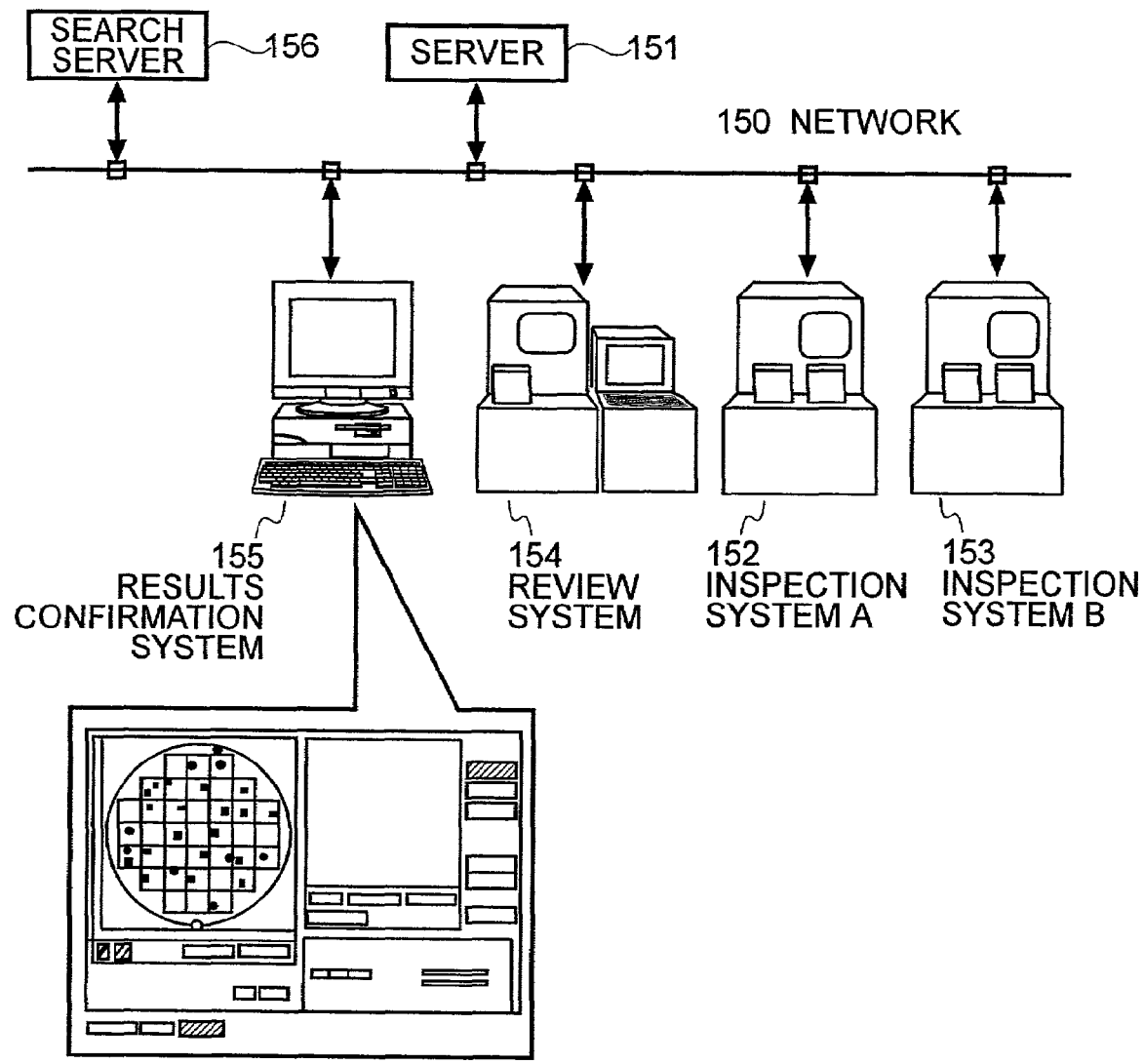
FIG. 6 is a diagram showing the overall constitution of a pattern inspection system according to the present invention.

The constitution of a first embodiment of the present invention is shown in FIG. 6. This first embodiment is constituted from a server 151, which is arranged on a network 150 and which manages and stores various information; an SEM (scanning electron microscope) type pattern inspection system, an optical type pattern inspection system, an extraneous material inspection system, a length-measuring SEM, and other such inspection systems A 152 and inspection systems B 153, which treat a target substrate 5 as an object, and inspect patterns and measure dimensions; a review system 154 for receiving inspection results from inspection system A 152 and inspection system B 153, fir positioning target substrate 5 at a specified defect location, and for visually checking this specified defect; and a defect checking system 155 for receiving and checking either inspection or measurement data at inspection time. The respective parts satisfy their functionality by operating as described hereinbelow.

That is, a target substrate is loaded, and either a pattern inspection or an extraneous material inspection is carried out, or pattern dimensions are measured by inspection system A 152 and inspection system B 153. Measurement results, together with image data of defective parts and measured portions are stored when inspection and measurement are performed, and the measurement results and image data are outputted over network 150. This data is stored in server 151 at one time.

Information of the measurement results and image data of a plurality of target substrate stored in server 151 is transmitted to defect review system 154, and measurement results are displayed on defect confirmation system 155. Based on the displayed results, image data of a defective portion, which is similar to the image of a specific defect, is retrieved using a method which will be explained hereinbelow, and the retrieval results are reflected on a display.

A first variation of this embodiment will be explained. That is, instead of executing a search via a defect checking system 155, a search can be executed via either inspection system A 152, or inspection system B 153, or server 151, or review system 154. Or, instead of the checking system 155, a search server 156, which is connected to the network 150, is provided, a search is executed by the search server 156, and only the results are displayed via a system other than defect checking system 155 or search server 156. Further, a search can be executed by an arbitrary system without the need to provide search server 156 independently.

(Inspection System)

Figure 7:
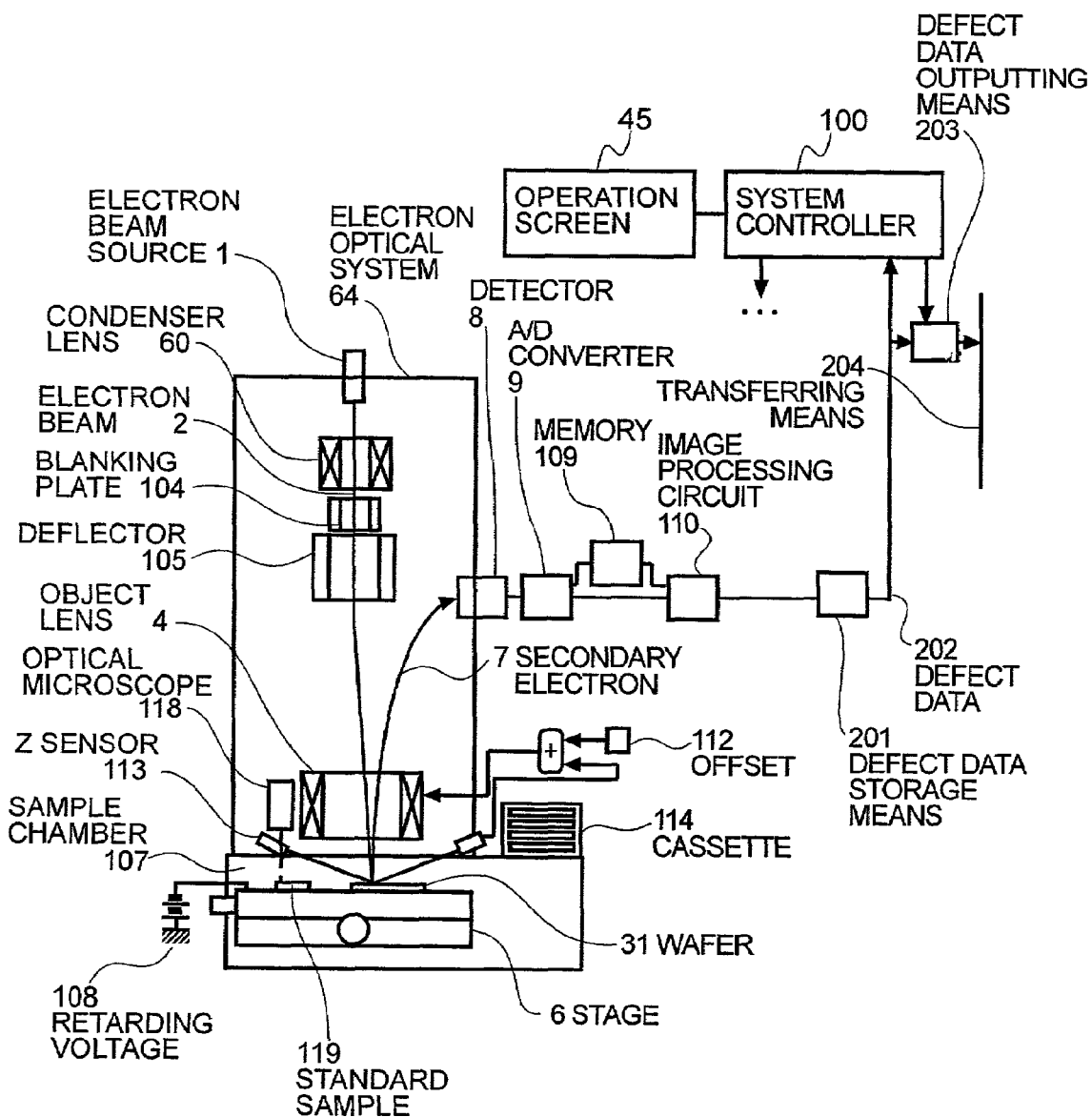
FIG. 7 is a schematic diagram showing a simplified constitution of an inspection system according to the present invention.

The constitution of a SEM-type pattern inspection system is shown in FIG. 7. This system comprises an electron beam source 1 having an electron gun for generating an electron beam 2; and an electron optical system 64 for accelerating and extracting the electron beam 2 from electron beam source 1 by means of an electrode, and which creates a virtual light source in a fixed location by means of an electrostatic or magnetic field superimposed lens. The electron optical system 64 includes a condenser lens 60 for converging the electron beam 2 from the virtual light source in a fixed location; a blanking plate 104, which is set near the convergence location, and which effects ON/OFF control of the electron beam 2 emitted from the electron gun; a deflector 105 for deflecting an electron beam 2 in XY directions; and an object lens 4 for converging the electron beam 2 onto a target substrate 5. A sample chamber 107 is evacuated for maintaining a wafer 31, which is the target substrate 5, in a vacuum; a stage 6, on which the wafer 31 is mounted, is located in the sample chamber 107, and a retarding voltage 108 is applied thereto for making it possible to detect an image of an arbitrary location. A detector 8 detects secondary electrons 7 emitted from target substrate 5; and an A/D converter 9 is provided for converting a signal detected by detector 8 from analog to digital and producing a digital image. A memory 109 is connected to the converter 9 for storing the digital image; and an image processing circuit 110 operates to compare data image stored in memory 109 with an A/D converted digital image and to detect the difference between the compared images as a pattern defect 11. A pattern defect storage portion 201, is provided for storing defect data 200, such as pattern defect 11 coordinates, projected length, area, critical threshold value DD (the threshold value at which, when the threshold value is lower than this value, a defect is detected), differential image average value, differential image distribution, maximum image difference, defect image texture, reference image texture, image of a defect portion, and a reference image having a pattern that is identical to that of the defect portion. Data outputting means 203 is connected to the pattern defect storage portion 201 for outputting stored defect data 200 to either a network or a storage medium. A system controller 100 is provided for controlling the entire system (control lines from system controller 100 are omitted from the figure); and a display unit is connected to the system controller 100. The display unit includes an operating screen 45 for performing various operations, a keyboard (not shown), a mouse (not shown) and a knob (not shown) for specifying operations. A Z sensor 113 is provided for maintaining the focal point position of a detected digital image constant by measuring the height of a wafer 31 and adding and controlling an offset 112 to the current value of object lens 4. A loader (not shown) is provided for loading and unloading wafers 31 carried in a cassette 114 into sample chamber 107; and an orientation flat detector (not shown) is provided for positioning the wafer 31 using the outline shape of the wafer 31 as a reference. An optical microscope 118 is provided for observing a pattern on the wafer 31; and a standard sample 119 is provided on stage 6.

Figure 1:
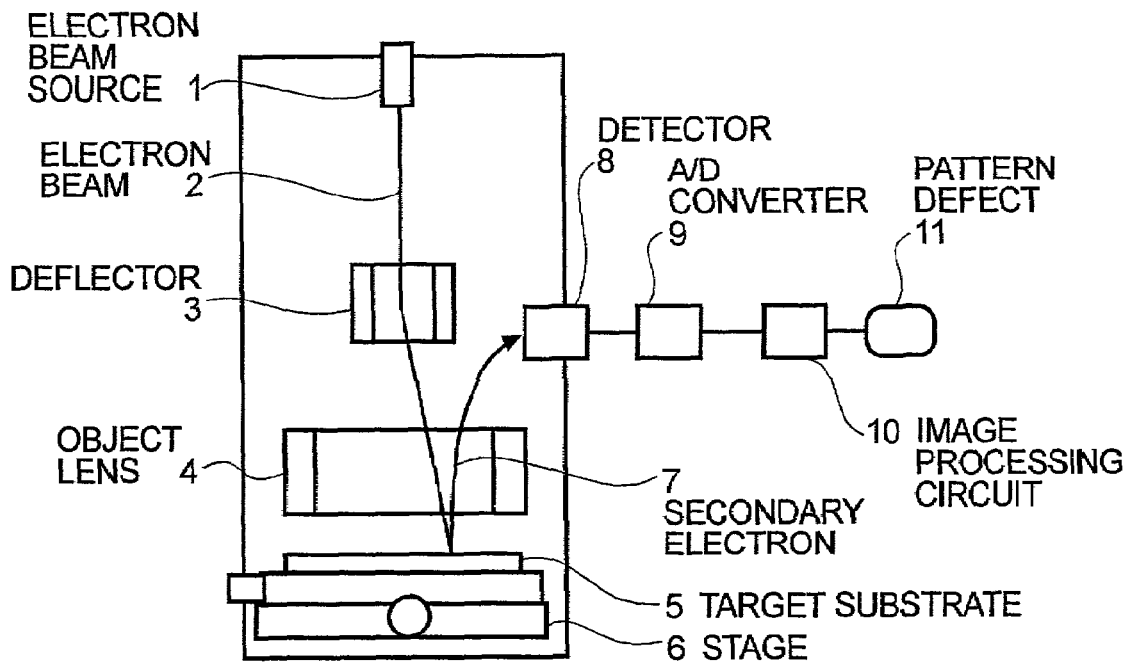
FIG. 1 is a schematic diagram showing a simplified constitution of a conventional electron beam-type pattern inspection system.
Figure 2:
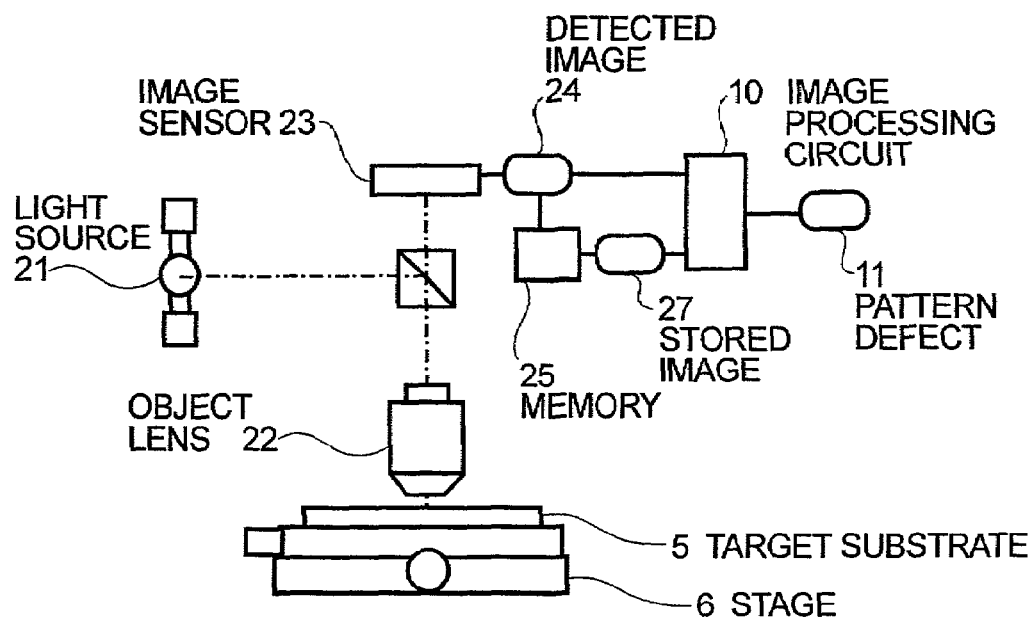
FIG. 2 is a schematic diagram showing a simplified constitution of a conventional optical-type pattern inspection system.
Figure 3:
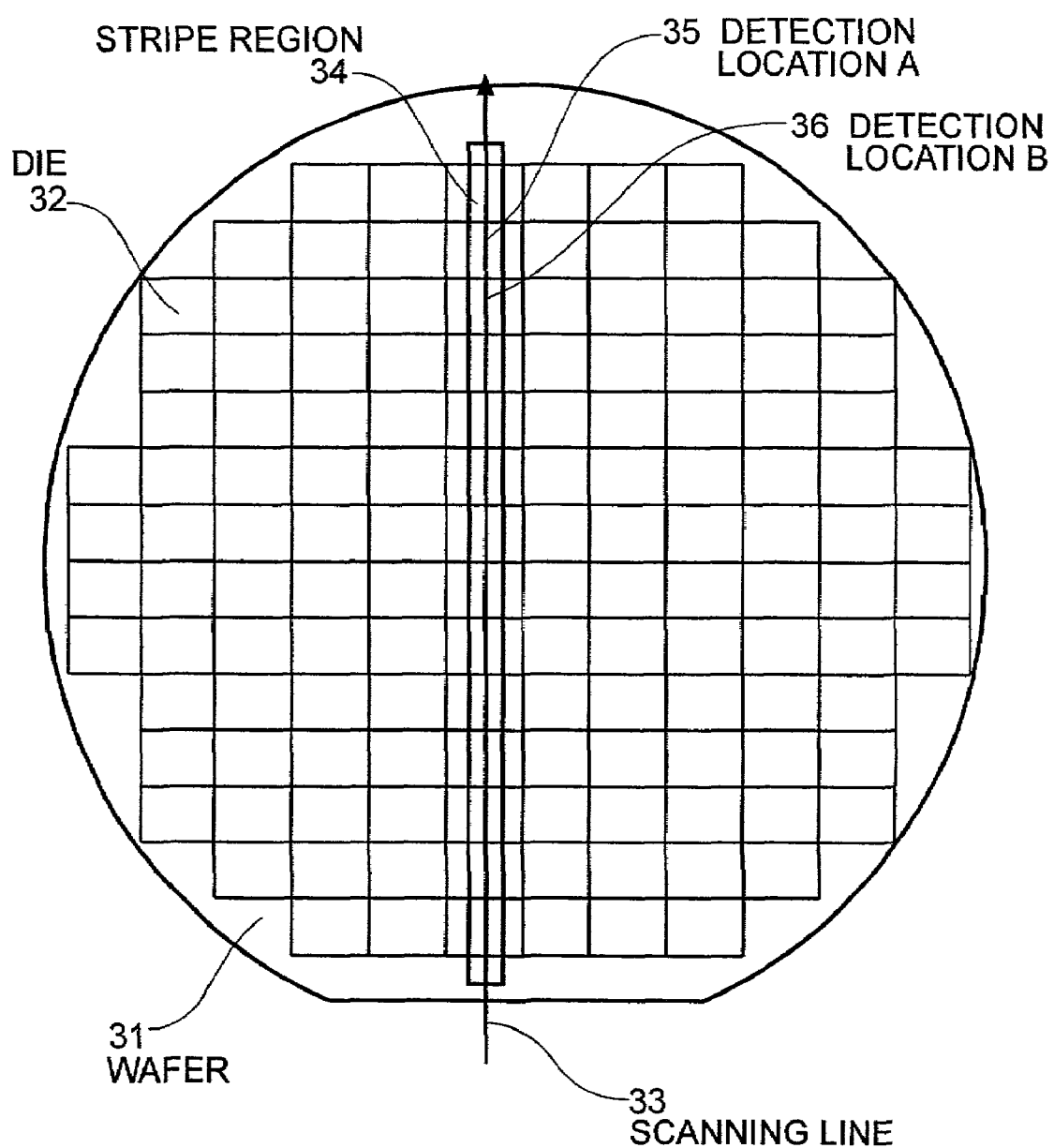
FIG. 3 is a plan view showing a wafer layout.

The operation of the inspection system will be explained. When an inspection is started by a command from a user, stage 6 moves and the region to-be-inspected on the wafer 31 mounted on the stage 6 is moved to the scanning start position. A wafer-specific offset measured beforehand is added and set in offset 112, Z sensor 113 is made operative, stage 6 scans in the Y direction along scanning line 33 shown in FIG. 3, deflector 105 scans in the X direction in synchronization with the scan of the stage, the voltage of blanking plate 104 is shut off at the effective scanning time, and an electron beam 2 is irradiated onto the wafer 31 and scanning is performed. Either reflected electrons or secondary electrons generated from wafer 31 are detected by detector 8, a digital image of stripe region 34 is produced by A/D converter 9, and this digital image is then stored in memory 109 and inputted in image processing circuit 110 in parallel. Upon termination of the scan of stage 6, Z sensor 113 is made inoperative.

An inspection of all required regions is carried out by repeating the scanning of the stage 6. When the detection is carried out in the location A 35 (Refer to FIG. 3), image processing circuit 110 compares a detected image of the location A 35 with an image of detection location B 36 (Refer to FIG. 3) stored in memory 109, and extracts a discrepancy between both images as a pattern defect 11, and the image of detection location A 36 is stored in defect data storage means 201. Defect data 200, such as extracted pattern defect 11 coordinates, projected length, area, critical threshold value DD (the threshold value at which, when the threshold value is lower than this value, a defect is detected), differential image average value, differential image distribution, maximum image difference, defect image texture, reference image texture, and image data, is stored in defect data storage means 201. And, from data outputting means 203, data is outputted as needed to data transferring means 204, which is either a network or an MO (magneto-optical disk), CDR (compact disk-recordable), DVD (digital video disk), FD (floppy disk) or other storage medium.

(Results Confirmation System)

Outputted defect data 202 is inputted via inputting means 205 (See FIG. 4) of results confirmation system 155 either via a network or from a storage medium, and defect location data from among the inputted defect data is displayed on defect map 207. When a specific item on the defect map is selected by selecting means 208, image data of the defect data is displayed in a image format on image displaying means 209. When a command is issued by search command means 210, a defect image similar to the display image is retrieved by image retrieving means 211 from among the defect data group, and retrieval results are reflected on defect map 207. Retrieval results can be checked as needed by issuing a command via selecting means 208. The frequency at which similar defects occur can be checked by displaying in the time-series format shown in FIG. 5, a display format of the defect map 207. In accordance therewith, the image data acquired at inspection time can be utilized effectively.

Figure 8:
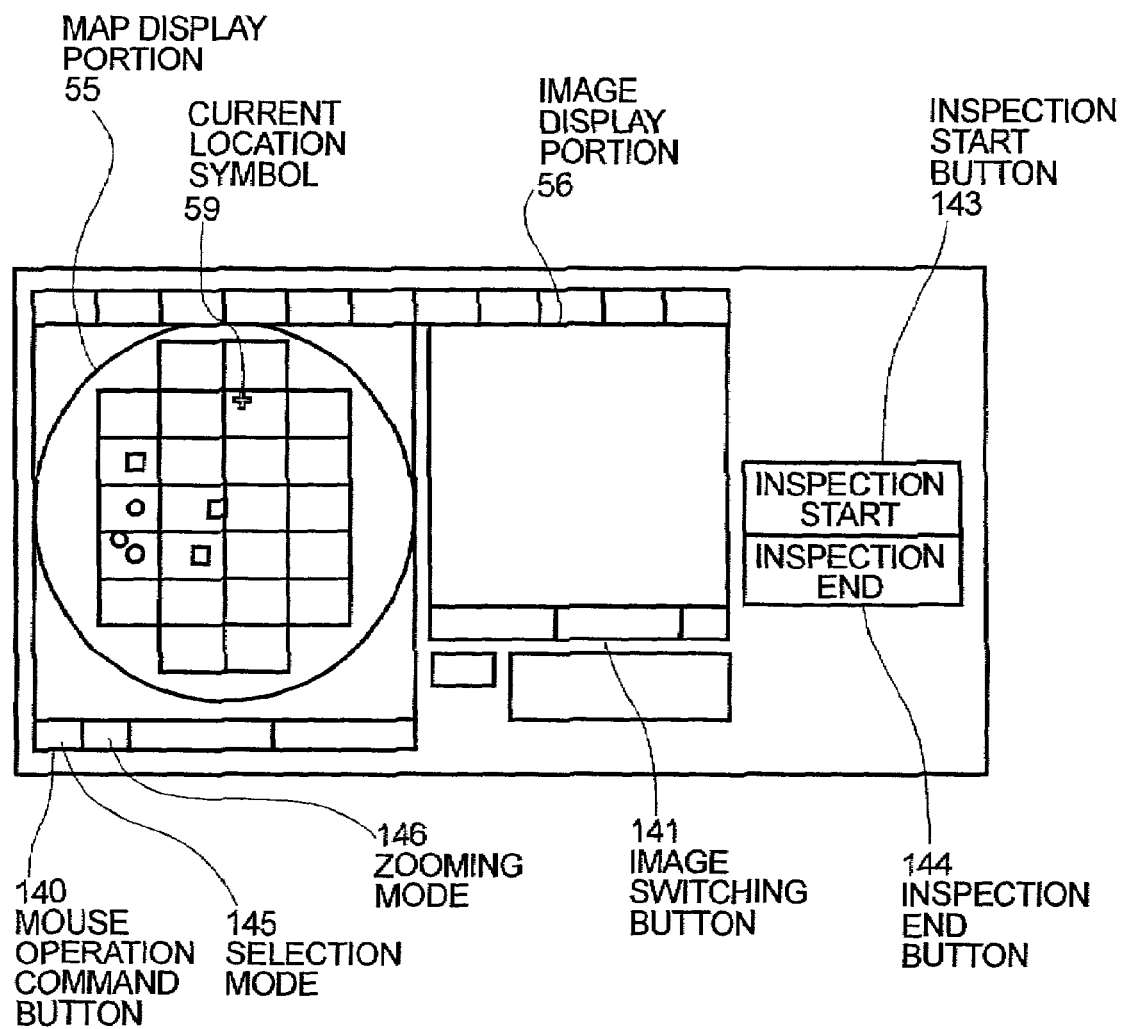
FIG. 8 is a diagram of a display screen showing an example of a results confirmation system according to the present invention.

An example of a display screen of the results confirmation system 155 is shown in FIG. 8. The location on a substrate (wafer) of each detected defect is displayed on map display portion 55, which corresponds to defect map 207 of FIG. 4.

Figure 4:
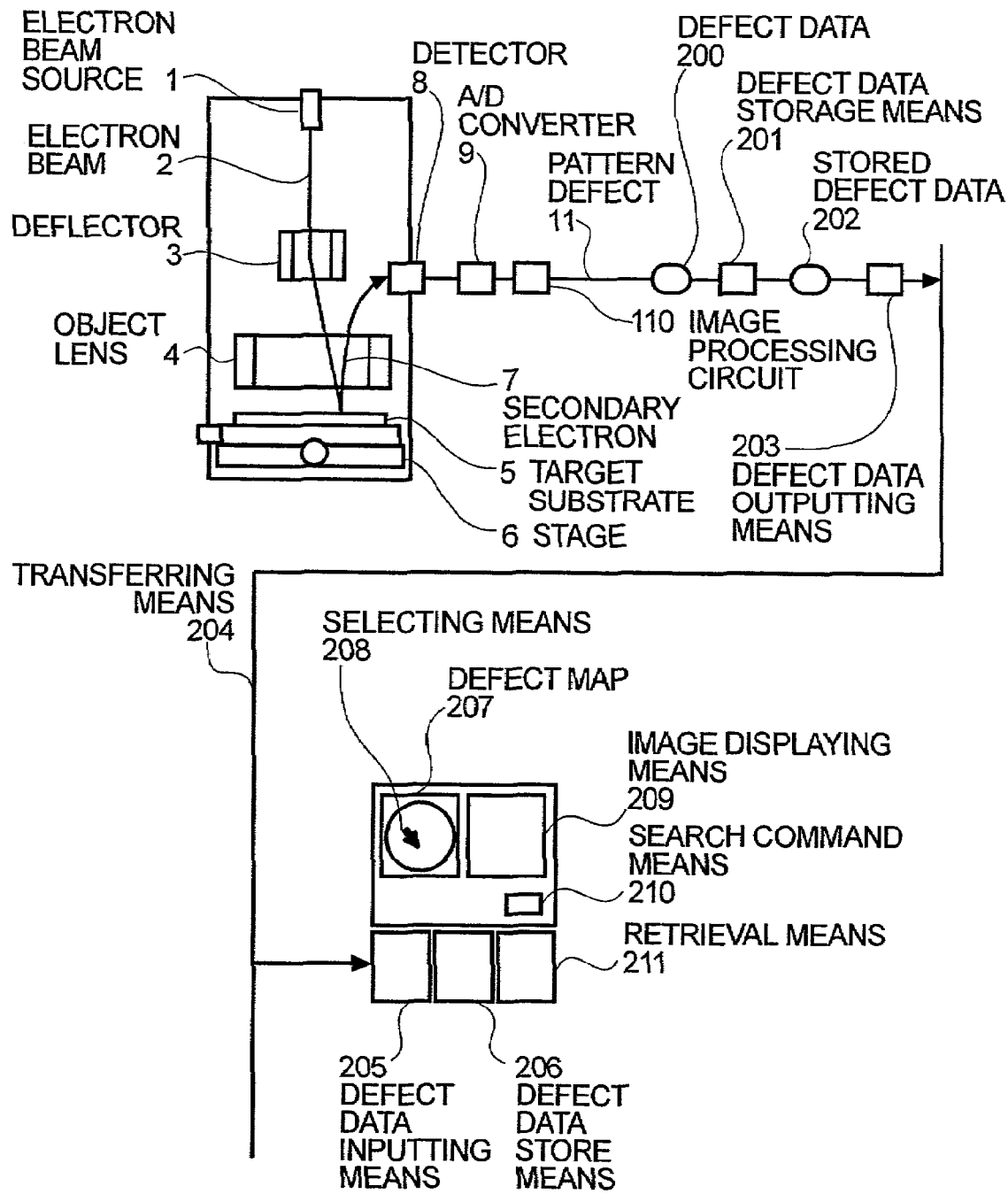
FIG. 4 is a schematic block diagram showing a simplified constitution of solution means of the present invention.
Figure 5:
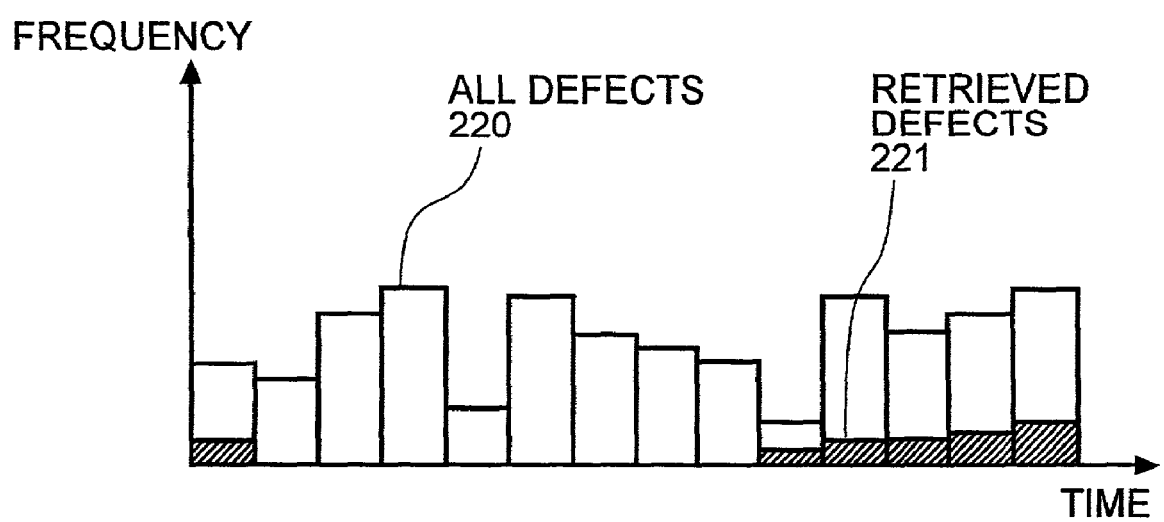
FIG. 5 is a graph showing an example of the occurrence frequency trends of defects.

Further, an image of a defect specified from among the defects displayed on the map display portion 55 is displayed on image display portion 56, which corresponds to image displaying means 209 of FIG. 4. Specifying a defect for displaying this image is effected by operating a mouse operation command button 140. That is, a current location symbol 59 is displayed on the screen using the mouse operation command button 140 to select a selection mode 145 from among a selection mode 145 and a zooming mode 146, the current location display 59 is moved with the mouse (not shown in the figure), and the image of a defect that a user wishes to see is displayed on image display portion 56 by clicking on the location of the defect to be viewed.

Further, when the zooming mode 146 is selected with the mouse operation command button 140, a display on map display portion 55 of the distribution of defects on a substrate can be either enlarged or reduced.

According to the present invention, an image of a defect portion, which is similar to an image of a defect portion specified on the basis of inspection results outputted by an inspection system and the defect portion image data thereof, is retrieved, and the conditions for the occurrence of a specific mode defect, which occurred in the past, can be identified by displaying the retrieval results so as to enable identification. Further, the present invention is characterized in that it enables the provision of functions for sounding an alarm in response to a future specific mode-generated defect by setting retrieval conditions in the inspection system.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An apparatus for inspecting a specimen, comprising:
   inspection means having a sensor to detect an actual image of a pattern formed on a specimen to be inspected and a processor to process the detected actual image to extract a defect candidate of the pattern with its location information;

output means for outputting an actual image of the extracted defect candidate and data including location information of the defect candidate;

information transfer means for transferring information outputted from the output means;

store means for storing information outputted from the output means and transferred by the information transfer means; and processing means having a display screen for processing the information stored in the store means and for displaying the processed information on the display screen;

wherein said processing means simultaneously displays defect candidate distribution data in a wafer map format on the display screen and an enlarged actual image of a defect candidate on the display screen.

2. The apparatus according to claim 1, wherein the processing means displays defect candidate location data on the display screen.

3. The apparatus according to claim 1, wherein the processing means displays a defect candidate location data in the map format on the display screen.

4. The apparatus according to claim 1, wherein the processing means classifies the defect candidates stored in the store means and displays the classified defect candidates on the display screen.

5. The apparatus according to claim 4, wherein the processing means displays the classified defect candidate actual image on the display screen.

6. The apparatus according to claim 4, wherein the processing means displays the classified defect candidates in the map format on the display screen.

7. An apparatus for inspecting a specimen, comprising:
an image detecting unit which detects actual images of a pattern formed on a substrate;
a defect candidate extracting unit which extracts a defect candidate from the detected actual images;
an outputting unit which outputs data of the extracted defect candidate including actual images of the extracted defect candidate;
a data storing unit which stores the outputted data from the outputting unit including actual images of the extracted defect candidate;
a processing unit which processes the stored data; and
a display unit which simultaneously displays data processed by the processing unit including defect candidate distribution data in a wafer map formed on a display screen and an enlarged actual image of a defect candidate side by side on the display screen.

8. An apparatus according to the claim 7, wherein said image detecting unit detects optical image of the pattern.

9. An apparatus according to the claim 7, wherein said image detecting unit detects secondary electron image of the pattern.

10. An apparatus according to the claim 7, wherein said defect candidate extracting unit extracts a defect candidate actual image and its location information from the detected actual images.

11. An apparatus according to the claim 7, wherein said defect candidate extracting unit extracts a defect candidate from the detected actual images by comparing the detected actual images with reference images.

12. An apparatus according to the claim 7, wherein said outputting unit and the data storing unit are connected by a network.

13. An apparatus according to the claim 7, wherein said processing unit detects defects among the stored defect candidates and the display unit displays an actual image of the extracted defect on the display screen.

14. An apparatus according to the claim 7, wherein said processing unit detects defects among the stored defect candidates and the display unit displays the detected defects in the map format on the display screen.

15. An apparatus according to the claim 7, wherein said processing unit detects defects among the stored defect candidates by using a variable threshold value.

16. An apparatus according to the claim 14, wherein said variable threshold value is determined on the display screen.

17. An apparatus for inspecting a specimen, comprising:
a defect candidate data processing unit for processing data of defect candidates including actual images of defect candidates which are detected by a detection machine and transferred through a communication line and stored in a memory; and
a display unit which simultaneously displays data processed by the defect candidate data processing unit including defect candidate distribution data in a wafer map format on a display screen and an enlarged actual image of a defect candidate which is one of the defect candidates displayed on the wafer map format on the display screen,
wherein the defect candidate data processing unit detect defects among the defect candidates by using a threshold value determined on the display screen of the display unit.

18. An apparatus according to the claim 17, wherein the defect candidate data processing unit classifies the defect candidate data and the display unit displays the classified defect candidate data on the display screen.

19. An apparatus according to the claim 17, wherein the map indicates distribution of the defect classified in the same category with the displayed defect actual image by the defect candidate data processing unit.

20. An apparatus according to the claim 17, wherein the display unit displays an actual image of defect which is pointed out on the map displayed on the display screen.

* * * * *